US008505557B1

(12) United States Patent
Urso

(10) Patent No.: US 8,505,557 B1
(45) Date of Patent: Aug. 13, 2013

(54) POWERED DENTAL CLEANER

(76) Inventor: Charles Louis Urso, Waltham, MA (US)

(*) Notice: Subject to any disclaimer, the term of this patent is extended or adjusted under 35 U.S.C. 154(b) by 132 days.

(21) Appl. No.: 13/065,730

(22) Filed: Mar. 29, 2011

(51) Int. Cl.
A61C 15/04 (2006.01)

(52) U.S. Cl.
USPC .............. 132/322; 132/323; 132/325

(58) Field of Classification Search
USPC ............. 132/321–327, 329, 309; 206/368, 206/63.5; 15/22.1, 22.2, 167.1, 167.2; 242/538, 538.1, 390.8, 402, 405, 588, 588.3
IPC .............. A61C 15/00; A45D 44/18; A46B 9/04
See application file for complete search history.

(56) References Cited

U.S. PATENT DOCUMENTS

| 1,225,955 | A |   | 5/1917  | Hickman       |         |
|-----------|---|---|---------|---------------|---------|
| 1,586,262 | A |   | 5/1926  | Noble         |         |
| 1,911,973 | A |   | 5/1933  | Ruse          |         |
| 2,282,700 | A |   | 5/1942  | Bobbroff      |         |
| 3,732,589 | A |   | 5/1973  | Burki         |         |
| 4,265,257 | A | * | 5/1981  | Salyer        | 132/322 |
| 4,586,521 | A | * | 5/1986  | Urso          | 132/322 |
| 4,706,695 | A | * | 11/1987 | Urso          | 132/322 |
| 4,738,271 | A | * | 4/1988  | Bianco        | 132/323 |
| 4,883,080 | A | * | 11/1989 | Lang          | 132/322 |
| 4,936,326 | A | * | 6/1990  | Eckroat       | 132/326 |
| 4,966,176 | A | * | 10/1990 | Lachenberg    | 132/325 |
| 5,184,632 | A | * | 2/1993  | Gross et al.  | 132/326 |
| 5,207,773 | A |   | 5/1993  | Henderson     |         |
| 5,224,500 | A |   | 7/1993  | Stella        |         |
| 5,315,732 | A | * | 5/1994  | Huefner et al.| 15/167.1|
| 5,323,796 | A |   | 6/1994  | Urso          |         |
| 5,406,664 | A | * | 4/1995  | Hukuba        | 15/22.1 |
| 5,560,378 | A | * | 10/1996 | Tiphonnet     | 132/325 |
| 5,722,440 | A | * | 3/1998  | Urso          | 132/323 |
| 5,762,078 | A | * | 6/1998  | Zebuhr        | 132/322 |
| 5,816,271 | A | * | 10/1998 | Urso          | 132/322 |
| 5,947,133 | A | * | 9/1999  | Kossak et al. | 132/323 |
| 6,874,509 | B2| * | 4/2005  | Bergman       | 132/325 |
| 7,011,099 | B2| * | 3/2006  | Bergman       | 132/325 |
| 7,255,111 | B2| * | 8/2007  | Chen          | 132/325 |
| 2003/0106565 | A1 | * | 6/2003 | Andrews     | 132/322 |
| 2003/0208870 | A1 | * | 11/2003 | Jimenez    | 15/167.1|
| 2004/0134511 | A1 | * | 7/2004  | Bergman    | 132/322 |
| 2007/0204879 | A1 | * | 9/2007  | Chen et al.| 132/325 |
| 2010/0139689 | A1 | * | 6/2010  | Couch      | 132/322 |
| 2010/0229888 | A1 | * | 9/2010  | Tiphonnet  | 132/322 |

* cited by examiner

*Primary Examiner* — Robyn Doan
*Assistant Examiner* — Tatiana Nobrega

(57) ABSTRACT

An embodiment of a dental flosser (10) includes a power driver (12) drivingly connectable to a flossing attachment (11). The flossing attachment includes a movably supported floss span (24) coming from a floss supply (26). A take-up spool (64) is positioned proximate to a floss-supporting tine (16) for winding used floss while fresh floss continually replaces the floss span. A cam (68) on the spool engages the tine to reciprocate the floss span for interdental cleaning. A brushing attachment (72) includes a resilient disk-shaped lingual brush (75) on a shaft (74). Opposite the lingual brush on the shaft is a resilient cup-shaped buccal brush (84). A spring (83) is positioned to urge the buccal brush to slide toward the lingual brush to engage and clean user teeth between the brushes. A brush lock (77) enables the brushes to be held apart for rinsing and air drying.

12 Claims, 2 Drawing Sheets

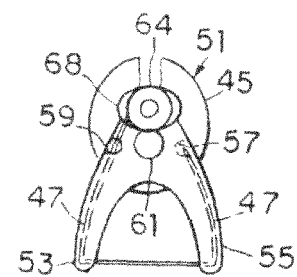
FIG. 3A
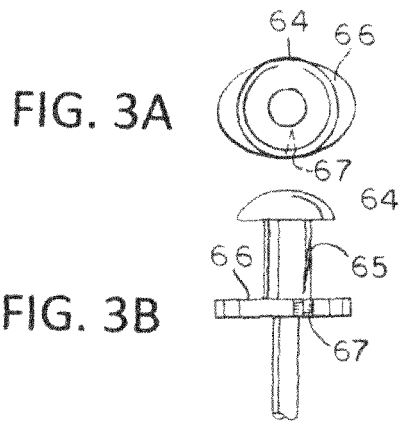
FIG. 3B
FIG. 4
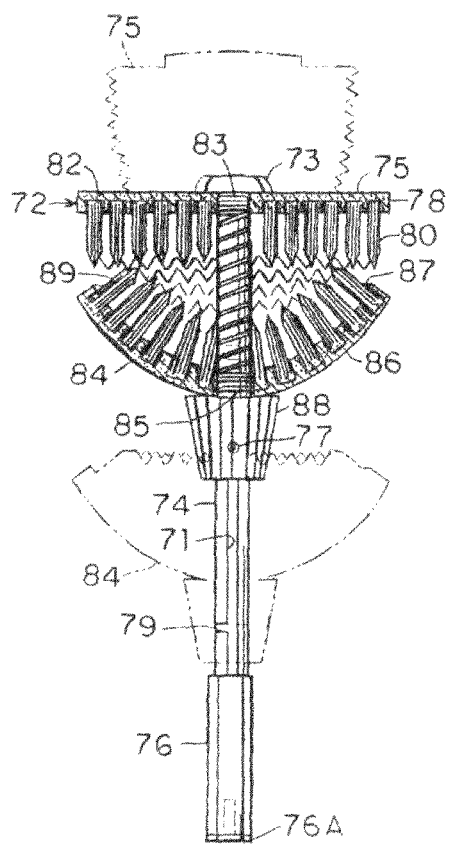
FIG. 5
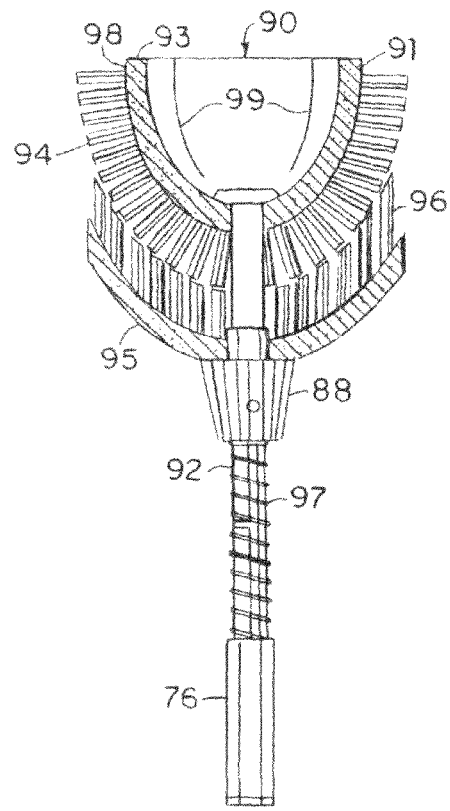
FIG. 6

POWERED DENTAL CLEANER

BACKGROUND

1. Field

This application relates to dental hygiene devices, specifically to powered dental flossers and powered tooth brushes.

2. Prior Art

Dental flossing is one of the most important personal hygiene tasks. Flossing contributes to the preservation of teeth, gum (gingival) tissues, jaw bones, and even general health. Yet, flossing is loathed by everyone because conventional methods are tedious, untidy, unpleasant, and inefficient. Conventional assistive devices on the market are less efficient then old-fashioned finger-manipulation of floss strands. Available floss-supporting frames provide little help. Changing floss spans on the frames is tedious and time consuming. Users of flossing frames typically use the same floss span for a plurality of teeth; an unhygienic practice. Some products power-rotate a tiny whip interdentally, but that method has little hygienic value. Proper interdental cleaning requires removal of adherent material from under circumferential gum lines wherein rotating a tiny whip is ineffective at getting under gum lines circumferentially.

The patent records show several powered flossers intended to provide continuous automatic floss replacement (CAFR) with some type of flossing action. But none have appeared on the market. A problem in common with CAFR flossers of record found and reviewed by this inventor is that used floss is dragged over portions of the flossers rearward of the flossing tines. This corrupts portions of the flossers that are difficult to sanitize and results in offensive odors.

With regard to powered tooth brushing, several types of powered tooth brushes are in the patent records wherein many have been commercialized. Each of the commercially available powered brushes, however, has a small brush head that can only brush a small area of a dental arch at a time. To use one, a user must direct the brush head to tooth surfaces sequentially on the inner, outer, and the top of all dentition in the mouth. The user must also keep track of which surfaces have been brushed and which have not been brushed in order to avoid missing tooth surfaces that need brushing; hence another burdensome process. The patent records show some proposed multi-head powered brushes for engaging more dental surfaces simultaneously than the commercialized brushes. But these proposed brushes, as presented in the patent literature, appear to be impractical. An IDS listing the most relevant examples of prior art CAFR flossers and multi-head brushes is forthcoming.

SUMMARY

Embodiments of a more practical dental cleaner, are shown and described in this application. They include CAFR flosser attachments that restrict used floss to a respective front end portion that enables easy sanitation of the cleaner with or without used floss thereon. Embodiments of powered brushing attachments each include a pair of opposed brushes shaped for conforming to a user's lingual and buccal surfaces, respectively. User dental arches between the brushes receive expedient power-cleaning. The embodiments are constructed from fewer elements than those of the prior art.

Advantages

Each CAFR flossing embodiment restricts movement and storage of used floss to a front end portion for economical sanitization with or without the used floss by insertion in a small amount of mouth wash. Fewer mechanical parts than those of the prior art achieve simultaneous longitudinal and transverse motions of a floss span. These motions work the span through tight spaces between teeth and under circumferential gum lines to remove debris. Disposal of used floss is expedited by protected floss cutters at expedient locations. Each powered brushing attachment brushes inner, outer, and top surfaces of dental arches and gums simultaneously while conforming to these surfaces to maximize surface contact. Other advantages of one or more aspects will be apparent from consideration of the drawings and ensuing description.

DRAWINGS—FIGS.

The accompanying drawings in combination with the description herewith illustrate features of some embodiments. Like reference numerals in different views refer to the same parts. The drawings are not necessarily to scale.

FIG. 3A is a front end view of a take-up spool and two-lobed cam from the cleaner of FIG. 1.

FIG. 3B is a side view of the take-up spool and two-lobed cam of FIG. 3A.

FIG. 4 is a front end view of a flossing attachment in accordance with another embodiment.

FIG. 5 is an enlarged side view of a brushing attachment shown partly in section taken through a longitudinal midline of the brushing attachment.

FIG. 6 is an enlarged side view of a brushing attachment in accordance with another embodiment and shown partly in section taken through a longitudinal midline of the brushing attachment.

DETAILED DESCRIPTION

Figures 1, 2:
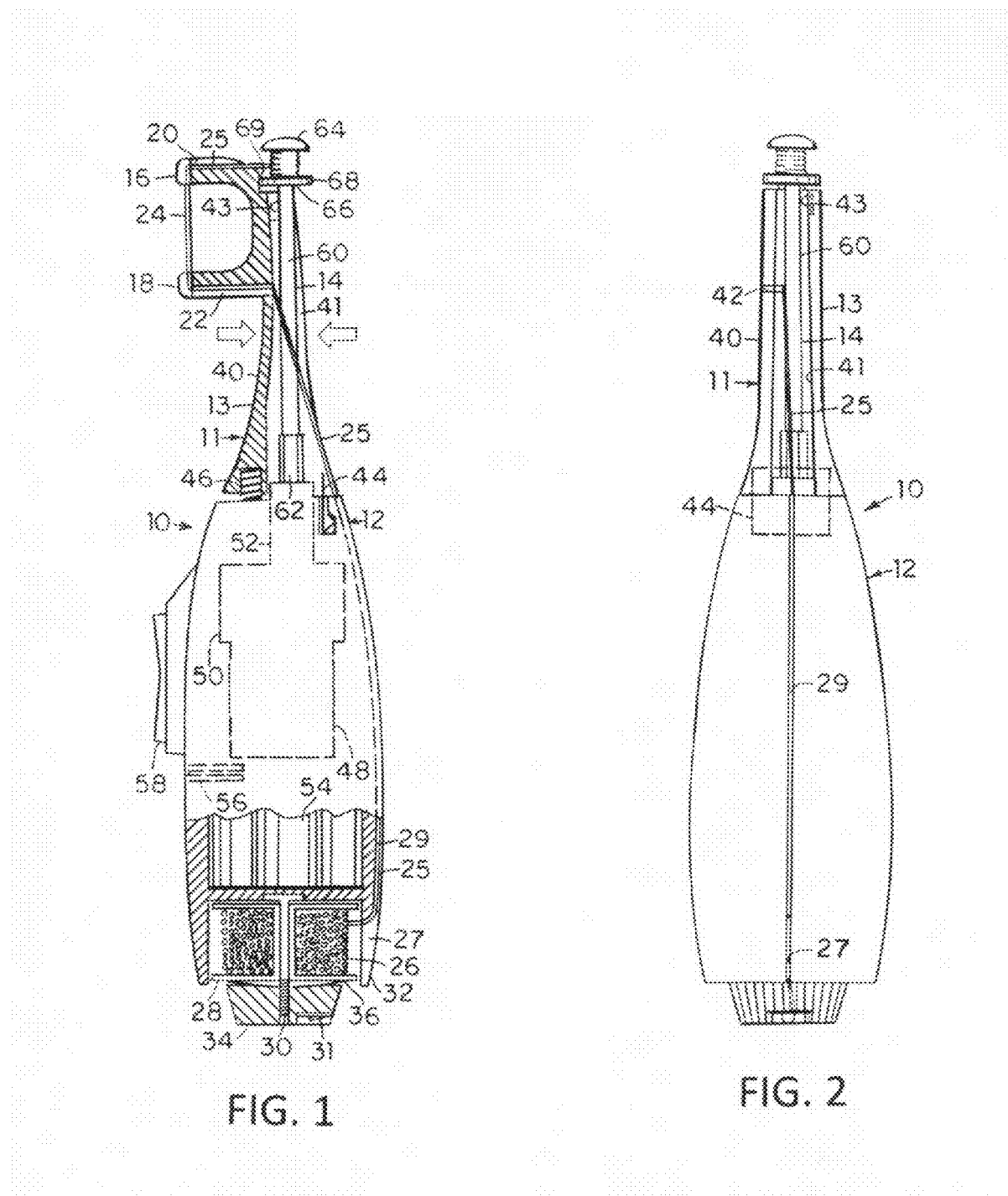
FIG. 1 is a lateral side view of a powered dental cleaner including a power driver detachably connected to a flossing attachment, both are shown partly in section taken through a longitudinal midline of the cleaner.
FIG. 2 is a top side view of the dental cleaner of FIG. 1.

First Embodiment—FIGS. 1, 2, 3A, and 3B

FIGS. 1 and 2 show an embodiment of a powered dental flosser 10 which includes a flossing attachment 11 detachably connected to a power driver 12. Except for modifications described herein, driver 12 is similar to a conventional mini-sized powered screwdriver. Conventional components include a reversible DC motor 48 (FIG. 1) drivingly connected to speed-reduction gears (not shown) contained in a gearbox 50 wherein the gears drive a magnetic hex socket 52 for rotation. Motor 48 is powered by rechargeable batteries 54 which can be recharged by a charger (not shown) when connected to a charging connector 56. Driver 12 is actuated by a mini double pole momentary On-Off momentary On rocker switch 58 which can operate driver 12 in forward or reverse rotation. A wiring circuit (not shown), operatively connecting the electrical components, is also conventional.

Flossing attachment 11 is comprised of two assemblies; an outer assembly 13 and an inner assembly 14. Assembly 13 includes a first flossing tine 16 positioned in front of a second flossing tine 18 wherein both are spaced from each other and positioned at a front end portion of flosser 10. Tines 16 and 18 define floss guide grooves 20 and 22, respectively, for guiding floss connected to a floss supply 26, thereby forming a movably supported floss span 24 between the tines. Groove 20 has proximal and distal ends. Similarly, groove 22 has proximal and distal ends. ("Proximal" in this case means near to where the subject tine is attached. "Distal" in this case means situated away from where the subject tine is attached.)

Tines 16 and 18 extend from and are supported by an arm 40 formed as a one-piece combination molded from plastic. Arm 40 is hollow and defines an open channel 41 (FIGS. 1 and 2) along its length which guides floss 25 to tines 18 and 16. A transverse semicircular slit 42 in arm 40 leads floss to tine groove 22 where the floss follows a floss route described hereinafter. A conventional floss cutter 43 is embedded in a recess inside arm 40 for cutting off used floss wherein cutter 43 is shielded by the outer surface of arm 40 for user safety.

Referring to FIG. 1, a flat spring 44 embedded in a base portion of arm 40 serves for detachably connecting assembly 13 to driver 12. To make the connection, a resilient end portion of spring 44, hook-shaped in cross-section, is inserted into a b-shaped cavity in the housing of driver 12. During the insertion, the hook-shape is squeezed until fully inserted wherein spring 44 snaps in place to complete the connection. Spring 44 is resiliently bendable and acts as a hinge pivotally supporting arm 40 and tines 16 and 18 for being reciprocated transversely of span 24. The white arrows in FIG. 1 indicate the directions of pivotal motion. A broad width of spring 44, as indicated in FIG. 2, restricts the pivotal motion to one plane. A compression spring 46 (FIG. 1), in a cylindrical cavity in the base portion of arm 40, urges arm 40 and its tines to pivot toward assembly 14 by pressing against a front wall of driver 12.

Assembly 14 includes a shaft 60 coaxially welded to a hex key 62 for being detachably received in socket 52. A front end portion of shaft 60 is coaxially fixed to a diminutive plastic take-up spool 64 by being press-fitted into a hub aperture in the spool core. Spool 64 is positioned to rotate at a location proximate to and directly over tine 16 as viewed when tines 16 and 18 are directed downwardly and the main body of driver 12 is horizontal. As shown in FIGS. 1 and 2, at least a portion of take-up spool 64 extends longitudinally beyond tines 16 and 18 such that the take-up spool defines a terminal distal end of the flosser.

Thus, used floss will be wound and restricted to the described location of spool 64 wherein bacteria on the used floss are prevented from spreading on the cleaner rearward of this location and the tines. Spool 64 is also directly over the proximal end of groove 20 as viewed when tines 16 and 18 are directed downward and the main body of driver 12 is horizontal. Thus, there can be a straight line perpendicular to the spool rotational axis and intersecting the spool core wherein the straight line is aligned with the proximal end of groove 20. This positioning of spool 64 insures proper winding even if groove 20 is other than straight.

Integrally molded with spool 64 is a flange 66 for retaining wound floss on the spool. Integrally molded with and extending radially from flange 66 is a two-lobed cam 68, thus being coaxially connected with spool 64. Cam 68 is arranged for drivingly reciprocating tines 16 and 18 to enhance the tooth cleaning action of floss span 24. Tine 16 includes a portion that forms and defines a cam follower 69 engaged by cam 68 to reciprocate tines 16 and 18. Thus, each rotation of spool 64 results in two reciprocation cycles of the tines because of the two lobes of cam 68. (If cam 68 were to have more than two lobes, such as three or four lobes, the number of reciprocation cycles of the tines would increase accordingly.)

As the tines and floss span 24 reciprocate transversely of the span while flossing a user's teeth, take-up spool 64 winds the floss used at span 24. In doing so, used floss is continuously replaced by fresh floss drawn through the floss route starting at floss supply 26 on a supply spool 28. From spool 28, floss 25 passes through a slit 27 in a rear end portion of a plastic driver housing 32. Floss 25 is then conveyed in a groove 29 that runs to the front end of housing 32. From there, floss 25 passes into channel 41 and to the bottom of slit 42, then through tine groove 22. After forming span 24, the floss is guided though tine groove 20 and onto spool 64. As indicated in FIGS. 3A and 3B, flange 66 defines a radial slit 67 wherein the core of spool 64 has an angular slit 65. Their functions are explained hereinafter.

A spindle 30 (FIG. 1), having a base imbedded in a rear wall of housing 32, rotatably supports spool 28. A tension control knob 34, having a hub aperture threaded to mate with a threaded end portion of spindle 30, engages a convex leaf spring 36 sandwiched between spool 28 and knob 34. A central aperture in spring 36 enables spindle 30 to pass through to mate with knob 34. As floss 25 is wound on spool 64, the tension of floss span 24 can be adjusted by turning knob 34. That is, by advancing knob 34 forward, spring 36 is increasingly compressed against spool 28 to increase its resistance to rotation, thereby increasing the tension of floss span 24. A conventional floss cutter 31 embedded in a recess in knob 34 serves for cutting off used floss after using flosser 10 for flossing as explained in the next section.

Operation of Driver 12 with Flossing Attachment 11

A user can initially install or mount floss in the system by drawing a few inches of floss 25 from supply spool 28 and running it along the floss route described above. To attach a floss end portion to spool 64, the user can draw the floss into core slit 65 (FIG. 3B) to hold the floss on the spool. If the free end portion of floss is longer than an inch, the user can draw the floss through flange slit 67 (FIG. 3A) which leads to adjacent floss cutter 43 where the excess floss can be expediently cut off. flosser 10 is then ready to use.

Pressing switch 58 (FIG. 1) starts rotation of spool 64 and cam 68 thereby reciprocating floss span 24 transversely thereof and moving longitudinally thereof as the span is continuously replaced. These motions work floss span 24 through tight spaces between teeth and under the gum lines to remove food debris. Light user pressure of span 24 against each tooth enables span 24 to wrap partway around the tooth being flossed for extensive cleaning by the powered transverse reciprocations and longitudinal motions.

When finished flossing, running flosser 10 for another few seconds insures that all used floss is wound onto spool 64. Hence, the used floss is restricted from contacting any portion of flosser 10 that is rearward of the tines. Running flosser 10 in reverse, while pulling span 24, empties spool 64. The used floss can then be cut off for disposal at cutter 43 or at cutter 31. While attachment 11 is mounted on driver 12, it can be rinsed under a running faucet. Open channel 41 enables the running water to flush the inside of attachment 11 and enables it to air dry. Alternatively, the user can postpone the removal of used floss and leave cleaner 10 ready to use. To do so, he can insert the front end portion of flosser 10, and its forward mounted floss-bearing spool 64, in a glass having an economically shallow amount of mouth wash. The spool location enables simple sanitization and sparing use of the antiseptic liquid.

Second Embodiment of Flossing Attachment—FIG. 4

FIG. 4 shows a front view of a second embodiment of a flossing attachment 51 which is similar to attachment 11 except for the differences described hereinafter. The main difference is that tines 53 and 55, extending from a plastic arm 45, are positioned side-by-side rather than one in front of the other as in attachment 11. Tine 55 defines a rear notch 57 forming a proximal end of a floss guide groove defined by tine 55. Tine 53 defines a front notch 59 forming a proximal end of a floss guide groove defined by tine 53.

Floss 47, from a supply spool, passes through arm 45 in the same manner as shown for floss 25 in arm 40. Then floss 47 enters notch 57 and the guide groove of tine 55 to span across to tine 53. From the floss guide groove of tine 53, floss 47 passes out of front notch 59 to be wound by spool 64. In this case, spool 64 is positioned to rotate at a location proximate to, frontally of, and directly over tines 53 and 55 as viewed when tines 53 and 55 are directed downward and the main body of the driver is horizontal. Thus, used floss will be wound and restricted to the described location of spool 64 wherein bacteria on the used floss are prevented from spreading on the flosser rearward of this location and the tines. Cam 68 drivingly engages a cam follower 61 which is a short cylinder extending from arm 45 and molded integrally together with arm 45 and tines 53 and 55. Hence, tines 53 and 55 and their associated floss span will be reciprocated transversely of the span when cam 68 rotates.

Brushing Attachment—FIG. 5

FIG. 5 shows a brushing attachment 72 detachably connectable to driver 12. Attachment 72 includes a plastic shaft 74 having a proximal end portion molded integrally and coaxially with a plastic hex key 76. Like key 62 of shaft 60, key 76 can be detachably inserted in magnetic driver socket 52. A ferrous cap 76A shaped like a flat-head screw is imbedded in the free end of key 76 for magnetic adhesion in driver socket 52. A distal or front end portion of shaft 74 is flanged to form a head 73 which is molded integrally with shaft 74 and key 76.

Head 73 is glued to a lingual brush 75 coaxially mounted on shaft 74. Brush 75 includes a flexible and resilient rubber lingual pad 78. Being normally disk-shaped, pad 78 defines a hub aperture that receives shaft 74. A face side of pad 78 is perforated with holes part way through the pad to receive a bristle tuft 80 in each hole. The bristles are made of flexible plastic wherein each tuft has a pointed distal end portion. To reinforce the integrity of bristle tufts 80, a base portion of each tuft is encapsulated in a conventional plastic bristle capsule 82. Each capsule 82 is glued to pad 78 at the bottom of its respective pad hole wherein the circular face of pad 78 is covered with an array of bristles extending therefrom in a direction rearward of attachment 72.

Opposing lingual brush 75 and coaxially mounted on shaft 74 is a buccal brush 84 constructed like brush 75 except for differences described hereinafter. Brush 84 includes a flexible and resilient circular buccal pad 86 similar to pad 78, but is normally cup-shaped. Pad 86 has a concave face 87 so that the combination can conform to the outer or buccal surfaces of dental arches and gum surfaces when urged against them. The distal end portions of its pointed bristle tufts 89 collectively form a cup-shape and are arranged in a concave pattern. As arranged, each bristle tuft 89 extends perpendicular to the surface of face 87 at the location from which the tuft extends. In general, the bristles of buccal brush 84 extend toward lingual brush 75.

Buccal brush 84 also includes a brush grip 88 glued to a central portion of pad 86. Grip 88 and pad 86 each define a central aperture, respectively, enabling brush 84 to be longitudinally slidable on shaft 74. Grip 88 is frustum-shaped with a narrow neck 85 projecting frontally. An extension spring 83, encircling shaft 74, has a rear end portion fixed to grip 88 by being tightly wound around neck 85. A front end portion of spring 83 is fixed to shaft 74 by being tightly wound around an annular grooved distal end portion of shaft 74. The main portion of spring 83 is of greater diameter and is slidably extendable on shaft 74. As arranged spring 83 urges brush 84 toward brush 75. Hence, buccal brush 84 is movable relative to lingual brush 75 along their axis. Under the pressure of spring 83, the bristles of both brushes will simultaneously engage user dental arches positioned between them for cleaning.

A longitudinal groove 71 in shaft 74 receives and guides a hub pin 77 passing through a transverse aperture in grip 88 to ensure that brush 84 will rotate together with shaft 74. Pin 77 can also be received in a transverse groove 79 around shaft 74 when a user turns grip 88 at that location. Thus, pin 77 can also serve as a lock for optionally retaining buccal brush 84 apart from lingual brush 75 against the urging of spring 83. The phantom image of brush 84 in FIG. 5 indicates the locked-open position wherein both brushes are separated and can receive toothpaste or all surfaces of both brushes can be rinsed clean and air-dried after use.

Operation of Driver 12 with Brushing Attachment 72—FIG. 5

Pulling or drawing grip 88 rearward against the tension of spring 83 will separate the brushes apart. Toothpaste can be applied to them and a user's dentition of both jaws can be inserted between the brushes by biting therebetween. In a user's mouth, lingual brush 75 will undergo changes in shape forced by the shape of the user's oral cavity. One likely shape is approximately that of a cup as indicated by the top phantom image of FIG. 5. Each shape of brush 75 will conform to the inner side (lingual side) of the teeth and gums of the upper and lower jaws that are engaged with brush 75. Buccal brush 84 will conform to the outer side (buccal side) of the engaged teeth and gums wherein brush 84 will adjust its shape accordingly. The bristles of both brushes together will also reach the biting surfaces of the teeth between them. By actuating driver 12 with rocker switch 58, the brushes can be rotated alternately clockwise and counterclockwise for cleaning wherein use of both directions is advantageous. Starting with the molars on one side of the mouth, bushing attachment 72 can be moved around the dental arches to the molars on the opposite side of the mouth. Brushing will be completed in substantially less time than with conventional powered brushes. When finished, attachment 72 should be locked with the brushes in the open (separated) position so that they can be rinsed under a running faucet and allowed to air dry.

Second Embodiment of a Brushing Attachment—FIG. 6

A second embodiment of a brushing attachment 90 (FIG. 6) is similar to attachment 72 except as explained hereinafter. A lingual brush 91 is coaxially fixed to a shaft 92 similar to shaft 74. A rubber flexible and resilient lingual pad 93 of brush 91 is normally cup-shaped and includes a convex outer face 98 with bristle tufts 94 extending from the outer face such that the combination is normally cup-shaped. The inner surface of pad 93 is concave so brush 91 will adjust to conform to the inner side of a user's dental arches, gum surfaces, and to the upper surface of the tongue. As arranged, each bristle tuft 94 extends perpendicular to the surface of face 98 at the location from which the tuft extends.

Pad 93 defines four equidistant divergent incisions 99 cutting thought the pad wall. Each incision 99 begins at a short distance from the shaft head and diverges away from shaft 92 to the mouth edge of the cup to form flower-like petals. When pad 93 is spinning, incisions 99 enable centrifugal force to spread the cup-shape of pad 93 and brush 91 radially toward becoming flatter. Thus, when rotating freely, pad 93 tends toward becoming disk-like in shape approximately like pad 78. Within an oral cavity, pad 93 will be cup-like when spinning, but centrifugal force spreading the cup-shape will increase bristle engagement with oral surfaces including teeth, gums, and tongue for a thorough cleaning.

A flexible and resilient buccal brush 95 is longitudinally slidable on shaft 92 and includes most of the features of buccal brush 84 except that the bristle tufts 96 are parallel to each other as they extend toward brush 91. Brush 95 is urged toward brush 91 by a compression spring 97 encircling shaft 92 and pushing between and against grip 88 and hex key 76.

It can be understood that any component of brushing attachment 90 can be exchanged with a corresponding component of brushing attachment 72. Compression spring 97, for example, could replace extension spring 83 wherein spring 97 would be positioned between grip 88 and hex key 76 of attachment 72.

SCOPE AND CONCLUSION

While the description above is of specific embodiments along with some of their uses and applications, these should not be construed as limitations on their scope, but rather as practical examples. Other embodiments are possible. For example, existing electronic components could be added to power driver 12 for automatically rotating one of the brushing attachments in alternating directions. Further, a lingual brush and buccal brush could be driven to rotate in opposite directions relative to each other by different shafts rotated coaxially, one within the other. A lingual brush could be shaped like buccal brush 84 or 95 less grip 88. In that case, the concave pad face and bristles would face the lingual side of teeth.

An alternative method of constructing each brush is to imbed base portions of bristle tufts in a rigid plastic pad similar in shape to a respective rubber pad described above. The plastic pad can be molded into 6 or 8 triangular pieces like a sliced pie. The pieces can be glued onto a rubber pad of the same shape and diameter as the plastic pad. The combination will be able to change shape like an umbrella.

With regard to the flossing attachment, the take-up spool and the attached cam could be separate elements driven to rotate by different shafts, respectively, rotating at different speeds relative to each other. The different shafts could be rotated coaxially, one within the other.

Driving two shafts having a common axis to rotate at different speeds, respectively, and/or rotate in opposite directions can be achieved by a driver having one motor and one gearbox modified by means known in the mechanical arts. An alternative modification is to add a gearshift switch to the driver that can shift the gears to turn socket 52 at selective speeds.

Thus the scope of the embodiments should be determined by the appended claims and their legal equivalents, rather than by the examples given.

I claim:

1. An elongate dental flosser, comprising:
   a motorized rotary driver including drive components and serving as a handle;
   a driven shaft extending longitudinally from a distal end of said motorized rotary driver;
   a pair of spaced flossing tines oriented substantially perpendicular to said driven shaft and supported at a front distal end portion of said flosser, said tines for supporting a movable floss span for engaging and cleaning teeth;
   a floss supply supporter for supplying fresh floss to said tines; and
   a rotatably supported take-up spool coupled to said driven shaft and positioned directly over one of said tines when viewed with the tines directed downwardly and said motorized rotary driver and driven shaft oriented horizontally, said rotatably supported take-up spool being flanged to retain spooled used floss and arranged for being power-driven to rotate by said driver to wind used floss coming from said tines,
   said spool being proximate to at least one of said tines such that immersion of said tines and take-up spool in the shallowest antiseptic liquid that covers said tines and said take-up spool allows for sanitation thereof.

2. The dental cleaner as defined in claim 1, further comprising a flat spring connected to said tines, said spring including a resilient hook-shaped end portion for being resiliently squeezed into a cavity defined by said driver for detachably connecting said tines pivotally to said driver.

3. The dental cleaner as defined in claim 1, wherein said tines are movably supported and said cleaner further includes a cam coaxially connected to said spool, said cam being arranged for drivingly reciprocating said tines to enhance tooth cleaning action of said floss.

4. The dental cleaner as defined in claim 3, wherein at least one of said tines includes a portion forming a cam follower for being engaged by said cam to reciprocate said tines.

5. The dental cleaner as defined in claim 1, wherein said tines are movably supported and said cleaner further includes a cam combined integrally with said spool and arranged for drivingly reciprocating said tines to enhance tooth cleaning action of said floss.

6. The dental flosser as defined in claim 1, wherein at least a portion of said take-up spool extends longitudinally beyond the pair of flossing tines to temporarily store used floss at a hygienically advantageous extremity of said flosser where said take-up spool defines a terminal distal end of said flosser.

7. The dental cleaner as defined in claim 1, wherein said spool includes a core and at least one of said tines defines a floss guide groove extending lengthwise thereof and directed to the middle of said spool core in proximate relation therewith for insuring proper winding of used floss around said core.

8. An elongate dental flosser, comprising:
   a motorized rotary driver including drive components and serving as a handle;
   a driven shaft extending longitudinally from a distal end of said motorized rotary driver;
   a pair of flossing tines oriented substantially perpendicular to said driven shaft and movably supported at a front distal end portion of said flosser, said tines for supporting a movable floss span for cleaning teeth;
   a floss supply supporter for supplying fresh floss to said tines; and
   a rotatably supported take-up spool arranged directly over one of said tines when viewed with said tines directed downwardly and said motorized rotary driver and driven shaft oriented horizontally, for winding used floss coming from said tines, said rotatably supported take-up spool provided with a rotatably supported cam said cam being coupled to and rotated by said driver in order to reciprocate said tines for enhancing tooth cleaning action of said floss.

9. The dental cleaner as defined in claim 8, wherein at least one of said tines supports a cam follower for being engaged by said cam in order to drivingly reciprocate said tines.

10. The dental cleaner as defined in claim 8, wherein said cam being integrally combined with said spool.

11. The dental cleaner as defined in claim 8, wherein said spool includes a core and at least one of said tines defines a floss guide groove extending longitudinally thereof and directed to the middle of said spool core in proximate relation therewith for insuring proper winding of used floss around said spool core.

12. The dental flosser as defined in claim 8, wherein each tine includes a proximal end and at least a portion of said take-up spool extends longitudinally beyond said pair of flossing tines such that the take-up spool defines a terminal distal end of the flosser.

\* \* \* \* \*